US007932268B2

(12) United States Patent
Rader

(10) Patent No.: US 7,932,268 B2
(45) Date of Patent: Apr. 26, 2011

(54) METHODS FOR TREATING DISORDERS OR DISEASES ASSOCIATED WITH HYPERLIPIDEMIA AND HYPERCHOLESTEROLEMIA WHILE MINIMIZING SIDE EFFECTS

(75) Inventor: Daniel J. Rader, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 895 days.

(21) Appl. No.: 10/591,923

(22) PCT Filed: Mar. 7, 2005

(86) PCT No.: PCT/US2005/007435
§ 371 (c)(1),
(2), (4) Date: Jun. 21, 2007

(87) PCT Pub. No.: WO2005/087234
PCT Pub. Date: Sep. 22, 2005

(65) Prior Publication Data
US 2009/0042941 A1    Feb. 12, 2009

Related U.S. Application Data

(60) Provisional application No. 60/550,915, filed on Mar. 5, 2004.

(51) Int. Cl.
*A61K 31/445* (2006.01)
(52) U.S. Cl. ........................... 514/321; 514/325
(58) Field of Classification Search .............. 514/252.03, 514/255.03, 263.22, 321, 325, 824, 210.02
See application file for complete search history.

(56) References Cited

U.S. PATENT DOCUMENTS

| | | | |
|---|---|---|---|
| 3,983,140 A | 9/1976 | Endo et al. | |
| 4,231,938 A | 11/1980 | Monaghan et al. | |
| 4,346,227 A | 8/1982 | Terahara et al. | |
| 4,448,784 A | 5/1984 | Glamkowski et al. | |
| 4,450,171 A | 5/1984 | Hoffman et al. | |
| 4,499,289 A | 2/1985 | Baran et al. | |
| 4,613,610 A | 9/1986 | Wareing | |
| 4,647,576 A | 3/1987 | Hoefle et al. | |
| 4,686,237 A | 8/1987 | Anderson | |
| 4,716,175 A | 12/1987 | Hoefle et al. | |
| 4,871,721 A | 10/1989 | Biller | |
| 4,924,024 A | 5/1990 | Biller | |
| 5,015,644 A | 5/1991 | Roth et al. | |
| 5,026,554 A | 6/1991 | Bartizal et al. | |
| 5,117,080 A | 5/1992 | Lee | |
| 5,510,379 A | 4/1996 | Lee et al. | |
| 5,595,872 A | 1/1997 | Wetterau, II et al. | |
| 5,684,014 A | 11/1997 | Muller et al. | |
| 5,712,279 A | 1/1998 | Biller et al. | |
| 5,712,396 A | 1/1998 | Magnin et al. | |
| 5,739,135 A * | 4/1998 | Biller et al. ............... 514/252.03 | |
| 5,760,246 A | 6/1998 | Biller et al. | |
| 5,767,115 A * | 6/1998 | Rosenblum et al. ...... 514/210.02 |
| 5,786,361 A | 7/1998 | Muller et al. | |
| 5,789,197 A | 8/1998 | Wetterau, II et al. | |
| 5,811,429 A | 9/1998 | Connell et al. | |
| 5,827,875 A | 10/1998 | Dickson, Jr. et al. | |
| 5,883,109 A * | 3/1999 | Gregg et al. .................. 514/321 |
| 5,885,983 A | 3/1999 | Biller et al. | |
| 5,952,498 A | 9/1999 | Lenfers et al. | |
| 5,990,110 A | 11/1999 | Firestone | |
| 6,034,115 A | 3/2000 | Connell et al. | |
| 6,057,339 A | 5/2000 | Gregg | |
| 6,066,650 A | 5/2000 | Biller et al. | |
| 6,066,653 A | 5/2000 | Gregg et al. | |
| 6,114,341 A | 9/2000 | Muller et al. | |
| 6,121,283 A | 9/2000 | Chang et al. | |
| 6,140,343 A | 10/2000 | DeNinno et al. | |
| 6,194,454 B1 * | 2/2001 | Dow .............................. 514/522 |
| 6,245,775 B1 | 6/2001 | Muller et al. | |
| 6,265,431 B1 | 7/2001 | Muller et al. | |
| 6,297,233 B1 | 10/2001 | Stein et al. | |
| 6,344,450 B1 | 2/2002 | Bisacchi et al. | |
| 6,479,503 B2 | 11/2002 | Muller et al. | |
| 6,492,365 B1 | 12/2002 | Wetterau, II et al. | |
| 6,498,156 B2 | 12/2002 | Glombik et al. | |
| 6,620,821 B2 | 9/2003 | Robl | |
| 6,627,636 B2 | 9/2003 | Robl | |
| 6,720,351 B2 | 4/2004 | Bertinato et al. | |
| 6,774,236 B1 | 8/2004 | Lenfers et al. | |

(Continued)

FOREIGN PATENT DOCUMENTS

AU    727895    7/1998

(Continued)

OTHER PUBLICATIONS

Catapano, Ezetimibe: a selective inhibitor of cholesterol absorption, European Heart Journal Supplements 2001 (3, Supplemental E): E6-E10).
Knopp RH, Drug treatment of lipid disorders. New England J. Med. 1999; 341(7): 498-511; electronic pp. 1-25.
Aggarwal, et al; BMC Cardiovasc. Disord. 27;5(1):30 (2005).
Chandler, et al., J. Lipid. Res. 44(10):1887-901 (2003).
Cuchel et al., "Inhibition of Microsomal Triglyceride Transfer Protein in Familial Hypercholesterolemia," N Engl J Med., (2007); 356:148-156.
Funatsu et al. "Atorvastatin Increases Hepatic Fatty Acid Beta-Oxidation in Sucrose-Fed Rats: Comparison with an MTP Inhibitor." Eur. J. Pharm. 2002 455:161-167.

(Continued)

Primary Examiner — Kevin Weddington
(74) Attorney, Agent, or Firm — Goodwin Procter LLP

(57) ABSTRACT

The present invention provides methods and compositions for treating hyperlipidemia and/or hypercholesterolemia comprising administering to the subject an effective amount of an MTP inhibitor to inhibit hyperlipidemia and/or hypercholesterolemia in said subject, wherein said administration comprises an escalating series of doses of the MTP inhibitor. In some embodiments the method comprises administering at least three step-wise, increasing dosages of the MTP inhibitor to the subject. In some embodiments, the method further comprises the administration of one or more other lipid modifying compounds.

8 Claims, No Drawings

U.S. PATENT DOCUMENTS

| | | | |
|---|---|---|---|
| 6,812,345 B2 | 11/2004 | Robl et al. |
| 6,846,836 B2 | 1/2005 | Hamann et al. |
| 6,858,622 B2 | 2/2005 | Muller et al. |
| 6,875,782 B2 | 4/2005 | Cheng et al. |
| 6,884,812 B2 | 4/2005 | Glombick et al. |
| 6,916,809 B2 | 7/2005 | Chen et al. |
| 6,916,813 B2 | 7/2005 | Atwal et al. |
| 6,949,572 B2 | 9/2005 | Bertinato et al. |
| 6,979,692 B2 | 12/2005 | Bertinato et al. |
| 7,053,080 B2 | 5/2006 | Davis et al. |
| 7,056,906 B2 | 6/2006 | Strony |
| 7,358,254 B2 | 4/2008 | Robl et al. |
| 7,394,501 B2 | 7/2008 | Iwata et al. |
| 7,645,732 B2 | 1/2010 | Ye et al. |
| 2002/0035064 A1 | 3/2002 | Robl et al. |
| 2002/0045271 A1 | 4/2002 | Hussain et al. |
| 2003/0069221 A1 | 4/2003 | Kosoglou et al. |
| 2003/0109543 A1 | 6/2003 | Ogletree |
| 2003/0153541 A1 | 8/2003 | Dudley et al. |
| 2003/0162788 A1 | 8/2003 | Thomas et al. |
| 2003/0187053 A1 | 10/2003 | Bertinato et al. |
| 2004/0014748 A1 | 1/2004 | Grutzmann et al. |
| 2004/0058908 A1 | 3/2004 | Keller et al. |
| 2005/0075367 A1 | 4/2005 | Hagiwara et al. |
| 2005/0090426 A1 | 4/2005 | Blumberg |
| 2005/0101561 A1 | 5/2005 | Tunac |
| 2006/0069161 A1 | 3/2006 | Lee et al. |
| 2006/0135460 A1 | 6/2006 | Widder et al. |
| 2006/0153913 A1 | 7/2006 | Yamane et al. |
| 2006/0160834 A1 | 7/2006 | Fong et al. |
| 2006/0166999 A1 | 7/2006 | Grutzmann et al. |
| 2006/0205726 A1 | 9/2006 | Hagiwara et al. |
| 2006/0211020 A1 | 9/2006 | Farrer et al. |
| 2006/0211762 A1 | 9/2006 | Rongen et al. |
| 2006/0252733 A1 | 11/2006 | Jansen |
| 2006/0270655 A1 | 11/2006 | Swick et al. |
| 2007/0027093 A1 | 2/2007 | Ogawa et al. |
| 2007/0032404 A1 | 2/2007 | Sweet et al. |
| 2007/0088089 A1 | 4/2007 | Wisler |
| 2007/0093468 A1 | 4/2007 | Wisler |
| 2007/0093527 A1 | 4/2007 | Wisler |
| 2007/0098778 A1 | 5/2007 | Borsadia |
| 2007/0099884 A1 | 5/2007 | Erondu et al. |
| 2008/0016127 A1 | 1/2008 | Field |
| 2008/0033019 A1 | 2/2008 | Stamler |
| 2008/0051427 A1 | 2/2008 | Schuckler |
| 2008/0103122 A1 | 5/2008 | Veltri |
| 2008/0161279 A1 | 7/2008 | Wisler |
| 2008/0175864 A1 | 7/2008 | Ye et al. |
| 2008/0241869 A1 | 10/2008 | Davis |
| 2008/0248070 A1 | 10/2008 | Tunac |
| 2008/0253985 A1 | 10/2008 | Wisler |
| 2008/0255084 A1 | 10/2008 | Webb |
| 2008/0280992 A1 | 11/2008 | Kunz et al. |
| 2009/0042835 A1 | 2/2009 | Davis |
| 2009/0042941 A1 | 2/2009 | Rader |
| 2009/0054393 A1 | 2/2009 | Wisler |
| 2009/0093527 A1 | 4/2009 | Li et al. |

FOREIGN PATENT DOCUMENTS

| | | |
|---|---|---|
| CA | 2091102 | 9/1993 |
| CA | 2291471 | 6/2000 |
| CA | 2325201 | 5/2001 |
| DE | 19951022 | 4/2001 |
| EP | 0142146 | 5/1985 |
| EP | 0221025 | 5/1987 |
| EP | 0325130 | 7/1989 |
| EP | 0705831 | 4/1996 |
| EP | 0779276 | 6/1997 |
| EP | 0779279 | 6/1997 |
| EP | 0799828 | 10/1997 |
| EP | 0802198 | 10/1997 |
| EP | 1099442 | 5/2001 |
| EP | 1 181 954 A | 2/2002 |
| FR | 2596393 | 10/1987 |
| GB | 2205837 | 12/1988 |
| JP | 2002-220345 | 8/2002 |
| WO | WO-86/03488 | 6/1986 |
| WO | WO-86/07054 | 12/1986 |
| WO | WO-96/26205 | 8/1996 |
| WO | WO-96/26948 A1 | 9/1996 |
| WO | WO-96/40640 | 12/1996 |
| WO | WO-97/41111 | 11/1997 |
| WO | WO-98/03069 | 1/1998 |
| WO | WO-98/03174 | 1/1998 |
| WO | WO-98/23593 | 6/1998 |
| WO | WO-98/27979 | 7/1998 |
| WO | WO-98/31225 | 7/1998 |
| WO | WO-98/31366 | 7/1998 |
| WO | WO-98/31367 | 7/1998 |
| WO | WO-98/50028 | 11/1998 |
| WO | WO-00/38725 | 7/2000 |
| WO | WO-01/08679 | 2/2001 |
| WO | WO-2004/028544 | 4/2004 |
| WO | WO-2004/110368 | 12/2004 |
| WO | WO-2004/110375 | 12/2004 |
| WO | WO-2005/000217 | 1/2005 |
| WO | WO-2005/033100 A1 | 4/2005 |
| WO | WO-2005/051382 | 6/2005 |
| WO | WO-2005/072740 | 8/2005 |
| WO | WO-2005/084666 | 9/2005 |
| WO | WO-2005/087234 | 9/2005 |
| WO | WO-2005/094864 | 10/2005 |
| WO | WO-2005/097131 | 10/2005 |
| WO | WO-2006/046623 | 5/2006 |
| WO | WO-2006/062748 | 6/2006 |
| WO | WO-2006/063128 | 6/2006 |
| WO | WO-2006/108666 | 10/2006 |
| WO | WO-2006/111238 | 10/2006 |
| WO | WO-2007/047724 | 4/2007 |
| WO | WO-2007/047880 | 4/2007 |
| WO | WO-2008/012056 | 1/2008 |
| WO | WO-2008/021353 | 2/2008 |
| WO | WO-2008/030382 | 3/2008 |
| WO | WO-2008/072061 | 6/2008 |
| WO | WO-2008/075949 | 6/2008 |
| WO | WO-2008/079398 A1 | 7/2008 |
| WO | WO-2008/090198 | 7/2008 |
| WO | WO-2008/115574 | 9/2008 |

OTHER PUBLICATIONS

Li, et al., "Discovery of Potent and Orally Active MTP Inhibitors as Potential Anti-Obesity Agents," Bioorganic & Medicinal Chemistry Letters, Oxford, GB, vol. 16, No. 11, Jun. 1, 2006, pp. 3039-3042.

Looije, Norbert A., et al., "Disodium Ascorbyl Phytostanyl Phosphates (FM-VP4) Reduces Plasma Cholesterol Concentration, Body Weight and Abdominal Fat Gain Within a Dietary-Induced Obese Mouse Model," Journal of Pharmacy & Pharmaceutical Sciences: A Publication of the Canadian Society for Pharmaceutical Sciences, vol. 8, No. 3, 2005, pp. 400-408.

Samaha, et al., "Inhibition Of Microsomal Triglyceride Transfer Protein Alone Or With Ezetimibe In Patients With Moderate Hypercholesterolemia," Nature Clinical Practice, (2008), pp. 1-9, Nature Publishing Group.

Atzel, A., et al., "Mechanism of Microsomal Triglyceride Transfer Protein Catalyzed Lipid Trasport", Biochemistry (1993), 32, 10444-10450.

Bakillah A. et al., "Decreased Secretion of ApoB follows inhibition of ApoB-MTP Binding by a Novel Antagonist", Biochemistry (Mosc), (2000) 39(16):4892-4899.

Barclay, "Hyperlipidemia", NMT Briefs, 2003.

Bayes, M., et al., "Gateways to Clinical Trials", Methods and Findings in Experimental and Clinical Pharmacology, 24(1):2002, 37-55.

Bays et al., "Pharmacotherapy for Dyslipidaemia—Current Therapies and Future Agents", Expert Opin Phamacother, Nov. 2003;4(11):1901-38.

Biller et al., "Isoprenoid (Phosphinylmethyl) Phosphonates as Inhibitors of Squalene synthetase", J. Med. Chem., 31 (10):1988, 1869-71.

Bruckert, "New Lipid-Modifying Therapies", Expert Opin. Investig. Drugs, (2003)12(3):325-35.

Capson, T.L., (Ph.D. Dissertation, Jun. 1987, Dept. Med. Chem. U. of Utah, Abstract).

Chang et al., "Microsomal Triglyceride Transfer Protein (MTP) Inhibitors: Discovery of Clinically Active Inhibitors Using High-Throughput Screening and Parallel Synthesis Paradigms", Current Opinion in Drug Discovery & Development, (2002) 5(4):562-70.

Corey and Volante, J. Am. Chem. Soc., (1976) 98:1291-93.

de Montellano et al., "Inhibition of Squalene Synthetase by Farnesyl Pyrophosphate Analogues" J. Med. Chem., (1977) 20:243-49.

Earl et al., "Ezetimibe", Nature Reviews, 2003, 2:97-98.

Evans M. et al. "Medical Lipid-Regulating Therapy: Current Evidence, Ongoing Trials and Future Developments", Drugs: 2004; 64 (11): pp. 1181-1196.

Expert Panel on Detection, Evaluation, and Treatment of High Blood Cholesterol in Adults. National Cholesterol Education Program; Adult Treatment Panell III Report. Publication No. 01-3095, I-1-IX-11. 2001. Bethesda, MD, National Heart, Lung, and Blood Institute.

Farrell., "Drugs and Steatohepatitis", Semin Liver Dis, (2002) 22(2):185-194.

Gagne, et al. "Efficacy and Safety of Ezetimibe Coadministered with Atorvastatin or Simvastatin in Patients With Homozygous Familial Hypercholesterolemia", Circulation, (2002) 105 (21):2469-75.

International Search Report for Application No. PCT/US05/07435 dated Jul. 14, 2005 (7 pages).

International Search Report for Application No. PCT/US06/040637 dated Jun. 12, 2007 (8 pages).

International Search Report for Application No. PCT/US06/040639 dated Jun. 12, 2007 (9 pages).

International Search Report for Application No. PCT/US06/040640 dated May 23, 2007 (9 pages).

International Search Report for Application No. PCT/US06/040953 dated Mar. 3, 2007 (8 pages).

Jamil et al., "An inhibitor of the Microsomal Triglyceride Transfer Protein Inhibits apoB Secretion From HepG2 Cells", Proc Natl Acad Sci U S A, (1996) 93(21):11991-11995.

Kastelein J., "What future for Combination Therapies", Int J. Clin Pract. Suppl. Mar. 2003; (134): pp. 45-50.

Kirkpatrick et al, "Market indicators", Nature, 2003, 2:98.

Liao et al., "Blocking Microsomal Triglyceride Transfer Protein Interferes with apoB Secretion Without Causing Retention or Stress in the ER", Journal of Lipid Research, (2003) 44(5):978.

McClard et al., J.A.C.S., (1987) 109:5544.

Ritter et al., "Heterocyclic Ring Scaffolds as Small-Molecule Cholesterol Absorption Inhibitors", Org. Biomol. Chem., 2005, 3:3514-3523.

Robl et al, "A Novel Series of Highly Potent Benzimidazole-Based Microsomal Triglyceride Transfer Protein Inhibitors", Journal of Medicinal Chemistry, 2001, 44(6):851-856.

Shiomi et al, "MTP Inhibitor Decreases Plasma Cholesterol Levels in LDL Receptor-Deficient WHHL Rabbits by Lowering the VLDL Secretion", Euro. Journal of Pharma. 2001, 431:127-131.

Sorbera, L.A., et al., Implitapide "Hypolipidemic Treatment of Atherosclerosis MTP Inhibitor ApoB Secretion Inhibitor", Drugs of the Future, (2000) 25(11):1138-1144.

Subhop et al., "Cholesterol Absorption Inhibitors For the Treatment of Hypercholesterolaemia", Drugs, 2002, 62(16):2333-2347.

Thomas et al., "Alleviation of MTP Inhibitor-Induced Hepatic Steatosis in Hyperlipidemic *fa/fa* Rats by Fenofibrate", Dept. of Metabolic Diseases and Dept. of Chemical Research, Boehringer Ingelheim Pharma GmbH & Co. KG., (2005).

Wetterau et al., "An MTP Inhibitor that Normalizes Atherogenic Lipoprotein Levels in WHHL Rabbits", Science, (1998) 282(5389):751-754.

Wetterau et al., "Microsomal Triglyceride Transfer Protein", Biochimica Biophysica Acta, (1997) 1345(2):136-150.

Wierzbicki A.S., "New Lipid-Lowering Agents", Expert Opinion on Emerging Drugs, Ashley Publications, GB, 8 (2):2003, 365-376.

* cited by examiner

METHODS FOR TREATING DISORDERS OR DISEASES ASSOCIATED WITH HYPERLIPIDEMIA AND HYPERCHOLESTEROLEMIA WHILE MINIMIZING SIDE EFFECTS

CROSS-REFERENCE TO RELATED APPLICATIONS

This application is a national phase application under 35 U.S.C. §371 of PCT/US05/007435 filed Mar. 7, 2005 which in turn claims priority benefit of U.S. Ser. No. 60/550,915, filed Mar. 5, 2004, all of which are hereby incorporated by reference in their entireties.

FIELD OF THE INVENTION

The present invention generally relates to therapy for hypercholesterolemia and hyperlipidemia.

BACKGROUND OF THE INVENTION

Hypercholesterolemia is a well-known risk factor for ASCVD, the major cause of mortality in the Western world. Numerous epidemiological studies have clearly demonstrated that pharmacological lowering of total cholesterol (TC) and Low-density Lipoprotein (LDL) Cholesterol (LDL-C) is associated with a significant reduction in clinical cardiovascular events. Hypercholesterolemia is often caused by a polygenic disorder in the majority of cases and modifications in lifestyle and conventional drug treatment are usually successful in reducing cholesterol levels. However, in few cases, as in familial hypercholesterolemia (FH), the cause is a monogenic defect and the available treatment in homozygous patients can be much more challenging and far from optimal because LDL-C levels remain extremely elevated despite aggressive use of combination therapy. Therefore, for this group of high-risk patients, effective medical therapy is urgently needed.

Triglycerides are common types of fats (lipids) that are essential for good health when present in normal amounts. They account for about 95 percent of the body's fatty tissue. Abnormally high triglyceride levels may be an indication of such conditions as cirrhosis of the liver, underactive thyroid (hypothyroidism), poorly controlled diabetes, or pancreatitis (inflammation of the pancreas). Researchers have identified triglycerides as an independent risk factor for heart disease.

Higher-than-normal triglyceride levels are often associated with known risk factors for heart disease, such as low levels of HDL ("good") cholesterol, high levels of LDL ("bad") cholesterol and obesity. Triglycerides may also contribute to thickening of artery walls—a physical change believed to be a predictor of atherosclerosis.

Therefore, high triglyceride levels are at least a warning sign that a patient's heart health may be at risk. In response, physicians may be more likely to stress the importance of losing weight, getting enough exercise, quitting smoking, controlling diabetes and other strategies that patients can use to protect their own cardiovascular health.

A large number of genetic and acquired diseases can result in hyperlipidemia. They can be classified into primary and secondary hyperlipidemic states. The most common causes of the secondary hyperlipidemias are diabetes mellitus, alcohol abuse, drugs, hypothyroidism, chronic renal failure, nephrotic syndrome, cholestasis and bulimia. Primary hyperlipidemias have also been classified into common hypercholesterolemia, familial combined hyperlipidemia, familial hypercholesterolemia, remnant hyperlipidemia, chylomicronemia syndrome and familial hypertriglyceridemia.

A number of treatments are currently available for lowering serum cholesterol and triglycerides. However, each has its own drawbacks and limitations in terms of efficacy, side-effects and qualifying patient population.

Bile-acid-binding resins are a class of drugs that interrupt the recycling of bile acids from the intestine to the liver; e.g., cholestyramine (Questran Light®, Bristol-Myers Squibb), and colestipol hydrochloride (Colestid®, The Upjohn Company). When taken orally, these positively-charged resins bind to the negatively charged bile acids in the intestine. Because the resins cannot be absorbed from the intestine, they are excreted carrying the bile acids with them. The use of such resins, however, at best only lowers serum cholesterol levels by about 20%, and is associated with gastrointestinal side-effects, including constipation and certain vitamin deficiencies. Moreover, since the resins bind other drugs, other oral medications must be taken at least one hour before or four to six hours subsequent to ingestion of the resin; thus, complicating heart patient's drug regimens.

The statins are cholesterol-lowering agents that block cholesterol synthesis by inhibiting HMGCoA reductase—the key enzyme involved in the cholesterol biosynthetic pathway. The statins, e.g., lovastatin (Mevacor®, Merck & Co., Inc.), simvastatin (Zocor®, Merck & Co., Inc.), atorvastatin (Lipitor®, Pfizer), rosuva (Crestor®, Astra Zeneca) and pravastatin (Pravachol®, Bristol-Myers Squibb Co.), and combinations thereof, are sometimes used in combination with bile-acid-binding resins. Statins significantly reduce serum cholesterol and LDL-serum levels, and slow progression of coronary atherosclerosis. However, serum HDL cholesterol levels are only moderately increased. The mechanism of the LDL lowering effect may involve both reduction of VLDL concentration and induction of cellular expression of LDL-receptor, leading to reduced production and/or increased catabolism of LDLs. Side effects, including liver and kidney dysfunction are associated with the use of these drugs (Physicians Desk Reference, Medical Economics Co., Inc., Montvale, N.J., 2004; hereinafter "PDR"). The FDA has approved atorvastatin to treat rare but urgent cases of familial hypercholesterolemia.

Ezetimibe is a cholesterol absorption inhibitor which reduces the amount of cholesterol absorbed by the body. Ezetimibe is used to reduce the amount of total cholesterol, LDL cholesterol (by about 18%), and apolipoprotein B. Ezetimibe is often used with a low cholesterol diet and, in some cases, other cholesterol lowering medications.

Niacin, or nicotinic acid, is a water soluble vitamin B-complex used as a dietary supplement and antihyperlipidemic agent. Niacin diminishes production of VLDL and is effective at lowering LDL. In some cases, it is used in combination with bile-acid binding resins. NIASPAN® has been approved to prevent recurrent heart attacks in patients with high cholesterol. Niacin can increase HDL when used at adequate doses, however, its usefulness is limited by serious side effects when used at such high doses.

Fibric acid derivatives ("fibrates") are a class of lipid-lowering drugs used to treat various forms of hyperlipidemia (i.e., elevated serum triglycerides) which may also be associated with hypercholesterolemia. Fibrates appear to reduce the VLDL fraction and modestly increase HDL. However, the effects of these drugs on serum cholesterol is variable. Fibrates are mainly used to lower high triglyceride levels. Although fibrates typically do not appear as effective as statins in lowering total cholesterol and LDL cholesterol levels, they are sometimes used in combination with statins or other medications to lower very high cholesterol levels. For example, fibrates are also sometimes added to statins to raise HDL cholesterol levels. In the United States, fibrates have been approved for use as antilipidemic drugs, but have not received approval as hypercholesterolemia agents. For example, clofibrate (Atromid-S®, Wyeth-Ayerst Laboratories) is an antilipidemic agent which acts to lower serum triglycerides by reducing the VLDL fraction. Although serum cholesterol may be reduced in certain patient subpopulations, the biochemical response to the drug is variable, and is not always possible to predict which patients will obtain favorable results. Atromid-S® has not been shown to be effective for prevention of coronary heart disease. The chemically and pharmacologically related drug, gemfibrozil (Lopid®, Parke-Davis) is a lipid regulating agent which moderately decreases serum triglycerides and VLDL cholesterol, and moderately increases HDL cholesterol—the $HDL_2$ and $HDL_3$ subfractions as well as both ApoA-I and A-II (i.e., the AI/AII-HDL fraction). However, the lipid response is heterogeneous, especially among different patient populations. Moreover, while prevention of coronary heart disease was observed in male patients between 40-55 without history or symptoms of existing coronary heart disease, it is not clear to what extent these findings can be extrapolated to other patient populations (e.g., women, older and younger males). Indeed, no efficacy was observed in patients with established coronary heart disease. Fenofibrate (Tricor, Secalip) is also used to reduce levels of cholesterol and triglycerides. Serious side-effects have been associated with the use of several fibrates including toxicity such as malignancy, (especially gastrointestinal cancer), gallbladder disease and an increased incidence in non-coronary mortality. Fibrates are often not indicated for the treatment of patients with high LDL or low HDL as their only lipid abnormality (Physician's Desk Reference, 2004, Medical Economics Co., Inc. Montvale, N.J.).

Oral estrogen replacement therapy may be considered for moderate hypercholesterolemia in post-menopausal women. However, increases in HDL may be accompanied with an increase in triglycerides. Estrogen treatment is, of course, limited to a specific patient population (postmenopausal women) and is associated with serious side effects including induction of malignant neoplasms, gall bladder disease, thromboembolic disease, hepatic adenoma, elevated blood pressure, glucose intolerance, and hypercalcemia.

Homozygous familial hypercholesterolemia (hoFH) is a serious life-threatening genetic disease caused by homozygosity or compound heterozygosity for mutations in the low density lipoprotein (LDL) receptor. Total plasma cholesterol levels are generally over 500 mg/dl and markedly premature atherosclerotic vascular disease is the major consequence. Untreated, most patients develop atherosclerosis before age 20 and generally do not survive past age 30. The primary goal of therapy consists of controlling the hypercholesterolemia to delay the development of atherosclerotic cardiovascular disease (ASCVD). However, patients diagnosed with hoFH are largely unresponsive to conventional drug therapy and have limited treatment options. A mean LDL-C reduction of only about 5.5% has been recently reported in patients with genotype-confirmed hoFH treated with the maximal dose of statins (atorvastatin or simvastatin 80 mg/day). The addition of ezetimibe 10 mg/day to this regimen resulted in a total reduction of LDL-C levels of 27%, which is still far from optimal. Several non-pharmacological options have also been tested. Surgical interventions, such as portacaval shunt and ileal bypass have resulted only in partial and transient LDL-C lowering. Orthotopic liver transplantation has been demonstrated to substantially reduce LDL-C levels in hoFH patients, but obvious disadvantages and risks are associated with this approach. Although hoFH could be an excellent model for gene therapy, this modality of treatment is not foreseeable in the near future due to the limitations on the availability of safe vectors that provide long-term expression of LDL receptor gene. Thus, the current standard of care in hoFH is LDL apheresis, a physical method of filtering the plasma of LDL-C which as monotherapy can transiently reduce LDL-C by about 50%. Apheresis uses affinity columns to selectively remove apoB-containing lipoproteins. However, because of rapid re-accumulation of LDL-C in plasma, apheresis has to be repeated frequently (every 1-2 weeks) and requires 2 separate sites for IV access. Although anecdotally this procedure may delay the onset of atherosclerosis, it is laborious, expensive, and not readily available. Furthermore, although it is a procedure that is generally well tolerated, the fact that it needs frequent repetition and IV access can be challenging for many of these young patients. Therefore, there is a tremendous unmet medical need for new medical therapies for hoFH.

Patients with heterozygous FH can usually be successfully treated with combination drug therapy to lower the LDL-C to acceptable levels. In contrast, hoFH is unresponsive to conventional drug therapy and thus there are limited treatment options. Specifically, treatment with statins, which reduce LDL-C by inhibiting cholesterol synthesis and upregulating the hepatic LDL receptor, have negligible effect in patients whose LDL receptors are non-existent or defective.

In July 2004, the NCEP published a paper entitled "Implications of Recent Clinical Trials for the National Cholesterol Education Program Adult Treatment Panel III Guidelines", updating certain elements of the "Adult Treatment Panel III (ATP III)" cholesterol guidelines released in 2001. For high-risk patients, individuals who have coronary heart disease (CHD) or disease of the blood vessels to the brain or extremities, or diabetes, or multiple (2 or more) risk factors that give them a greater than 20 percent chance of having a heart attack within 10 years, the ATP III update recommends that the overall goal for high-risk patients is still an LDL less than 100 mg/dL with a therapeutic option to set the goal at an LDL less than 70 mg/dL for very high-risk patients, those who have had a recent heart attack, or those who have cardiovascular disease combined with either diabetes, or severe or poorly controlled risk factors (such as continued smoking), or metabolic syndrome (a cluster of risk factors associated with obesity that includes high triglycerides and low HDL cholesterol). The ATP III update also recommends consideration of drug treatment in addition to lifestyle therapy for LDL levels 100 mg/dL or higher in high-risk patients, and characterizes drug treatment as optional for LDL less than 100 mg/dL. For moderately high-risk patients, individuals who have multiple (2 or more) CHD risk factors together with a 10-20 percent risk for a heart attack within 10 years, the ATP III update recommends the overall goal for moderately high-risk patients to be an LDL less than 130 mg/dL. There is a therapeutic option to set the treatment goal at an LDL less than 100 mg/dL, and to use drug treatment if LDL is 100-129 mg/dL. For high-risk and moderately high-risk patients, the ATP III update advises that the intensity of LDL-lowering drug treatment in high-risk and moderately high-risk patients be sufficient to achieve at least a 30 percent reduction in LDL levels.

Patients suffering from severe hypercholesterolemia may also be unable to reach the new goals for LDL and HDL described above. For example, a large number of patients may be unable to attain LDL levels less than 70 using maximally tolerated current methodologies.

Abetalipoproteinemia is a rare genetic disease characterized by extremely low cholesterol and TG levels, absent apolipoprotein (apo) B-containing lipoproteins in plasma, fat malabsorption, severe vitamin E deficiency, and progressive spinocerebellar and retinal degeneration. It has been determined that mutations in the MTP were the genetic cause of abetalipoproteinemia. MTP is responsible for transferring lipids, particularly TG, onto the assembling chylomicron and VLDL particles in the intestine and the liver, respectively. Although the mechanisms by which lipoproteins are formed are not completely understood, it is currently believed that the assembly of apoB containing lipoproteins requires two steps. The first step occurs within the endoplasmic reticulum that involves the synthesis of particles that contain only a small fraction of the lipid core found in the secreted lipoprotein. A larger core of lipid is added to the nascent particle in a second step. MTP is thought to be essential for the transfer of lipid to the apoB during the first step of the process. In the absence of functional MTP, chylomicrons and VLDL are not effectively assembled or secreted in the circulation and apoB is likely targeted for degradation. VLDL serves as the metabolic precursor to LDL and the inability to secrete VLDL from the liver results in the absence of LDL in the blood. The concept that MTP may regulate apoB lipoprotein assembly is supported by observations in mice models. In heterozygous knockout mice MTP mRNA, protein and activity have been reported approximately half of normal and the apoB plasma concentration was reduced about 30%. Dramatic reduction of apoB-100 concentration in plasma was also seen in liver-specific MTP knockout mice. The finding that MTP is the genetic cause of abetaliproteinemia and that is involved in apoB-containing particles assembly and secretion led to the concept that pharmacologic inhibition of MTP might be a successful strategy for reducing atherogenic lipoproteins levels in humans.

Because of the tremendous impact on the treatment of atherosclerosis and cardiovascular disease that can be derived from the pharmacologic inhibition of hepatic secretion of apoB containing lipoproteins, several MTP inhibitors have been developed. Both in vitro and in vivo animal studies with these compounds support the concept that inhibition of MTP results in inhibition of apoB containing lipoproteins secretion and consequent reduction of plasma cholesterol levels. Interestingly, the animal studies cited above had been conducted in Watanabe-heritable hyperlipidemic (WHHL) rabbits and LDLR-/-mice, two models for hoFH.

Bristol-Myers Squibb (BMS) developed a series of compounds, including BMS-201038, as potent inhibitors of MTP-mediated neutral lipid transfer activity. These compounds are described, for example, in U.S. Pat. Nos. 5,789,197, 5,883,109, 6,066,653, and 6,492,365, each of which is incorporated herein by reference in its entirety. MTP inhibitors are described throughout U.S. Pat. No. 6,066,653, in particular in columns 3-28. In in vitro studies, BMS-201038 appears to inhibit lipid transfer by directly binding to MTP. In cell culture studies, the $IC_{50}$ for inhibition of apoB secretion by BMS-201038 was much lower than that for apoAI secretion (0.8 nM vs 6.5 µM), indicating that the compound is a highly selective inhibitor of apoB secretion. The efficacy to inhibit accumulation of triglyceride-rich particles in plasma of rats after injection of Triton is similar in both fed and fasted states, suggesting that both intestinal and hepatic lipoprotein secretions are inhibited by this compound. Six-month toxicity studies were conducted by BMS in rats and dogs and their results are detailed in IND# 50,820. Doses tested were 0, 0.02, 0.2, 2.0, and 20 mg/kg in rats and 0, 0.01, 0.1, 1.0, and 10 mg/kg in dogs. Dose-related lipid accumulation in the liver and small intestine correlated with decrease in serum TG and cholesterol levels. These changes are a consequence of the pharmacologic effects of BMS-201038. In rats, but not in dogs, doses of 0.2 mg/kg and higher were associated with subacute inflammation and single-cell necrosis of hepatocytes and histiocytosis (phospholipidosis) in the lungs. The hepatic accumulation of lipids was reversed in rats at the end of a 1-month washout period. Studies in animals indicated that BMS-201038 effectively reduced plasma cholesterol levels in a dose dependent manner. BMS-201038 was found to be effective in reducing cholesterol levels in rabbits that lack a functional LDL receptor: The $ED_{50}$ value for lowering cholesterol was 1.9 mg/kg and a dose of 10 mg/kg essentially normalized cholesterol levels with no alteration in plasma AST or ALT. This study, conducted in the best accepted animal model for the homozygous FH, indicated that MTP inhibition by BMS-201038 might be effective in substantially reducing cholesterol levels in patients with hoFH.

Clinical development of BMS-201038 as a drug for large scale use in the treatment of hypercholesterolemia has been discontinued, because of significant and serious hepatotoxicities. For example, gastrointestinal side effects, elevation of serum transaminases and hepatic fat accumulation were observed, primarily at 25 mg/day or higher doses. Thus, there is a need to develop methods for treating hyperlipidemia and/or hypercholesterolemia that are efficacious in lowering serum cholesterol and LDL, increasing HDL serum levels, preventing coronary heart disease, and/or treating diseases associated with hyperlipidemia and/or hypercholesterolemia, without the side-effects associated with known treatments.

SUMMARY OF THE INVENTION

The present invention relates to methods of treating disorders associated with hypercholesterolemia and/or hyperlipidemia.

In some embodiments the invention relates to methods of treating a subject suffering from a disorder associated with hyperlipidemia and/or hypercholesterolemia. The methods comprise administering to the subject an amount of an MTP inhibitor effective to ameliorate the disorder, wherein said administration comprises at least three step-wise, increasing dosages of the MTP inhibitor. In some embodiments the MTP inhibitor has the structure:

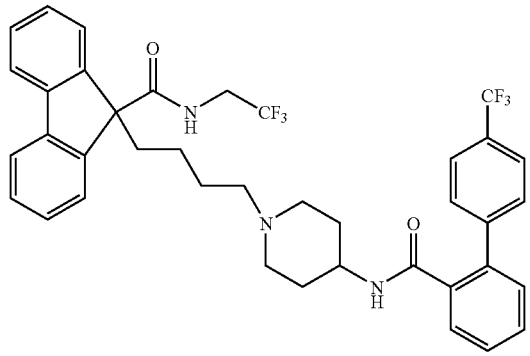

or a pharmaceutically acceptable salt thereof or the piperidine N-oxide thereof.

The present invention further provides methods for inhibiting MTP in a subject in need thereof. The methods comprise administering to the subject an amount of an MTP inhibitor effective to inhibit MTP, wherein said administration comprises at least three step-wise, increasing dosages of the MTP inhibitor.

The present invention provides kits for treating a disorder associated with hyperlipidemia and/or hypercholesterolemia in a subject, comprising at least three sets of pharmaceutical dosage units; and instructions for use.

DETAILED DESCRIPTION OF THE INVENTION

The present invention is based on the surprising discovery that one may treat an individual who has hyperlipidemia and/or hyperlcholesterolemia with an MTP inhibitor in a manner that results in the individual not experiencing side-effects normally associated with the inhibitor, or experiencing side-effects to a lesser degree. Accordingly, the present invention provides methods of treating a subject suffering from a disorder associated with hyperlipidemia while reducing side-effects, the method comprising the step of administering to the subject an effective amount of the MTP inhibitor to ameliorate hyperlipidemia and/or hypercholesterolemia in the subject according to a treatment regimen that reduces and/or eliminates side-effects associated with the use of the inhibitors.

By "treatment" is meant at least an amelioration of the symptoms associated with the pathological condition afflicting the host as well as an amelioration of the side-effects associated with the MTP inhibitor seen in patients treated in accordance with traditional treatment regimens making use of MTP inhibitors. "Amelioration" is used in a broad sense to refer to at least a reduction in the magnitude of a parameter, e.g. symptom, associated with the pathological condition being treated, such as elevated plasma VLDL or triglyceride levels, or with a side effect of treatment using the inhibitor, such as GI side-effects or hepatobiliary side-effects. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition, e.g. plasma VLDL and/or triglyceride levels are returned to normal.

The present invention also provides methods of treating diseases/disorders associated with hypercholesterolemia and/or hyperlipidemia comprising administering to a subject an MTP inhibitor and a further lipid modifying compound. The methods reduce and/or eliminate side-effects associated with the use of MTP inhibitors.

As used herein, the phrase "disorders associated with hyperlipidemia and/or hypercholesterolemia" refers to diseases and disorders related to or caused by elevated lipid or cholesterol levels. Such diseases and disorders include, without limitation, hypercholesterolemia, severe hypercholesterolemia, familial combined hyperlipidemia, familial hypercholesterolemia, remnant hyperlipidemia, chylomicronemia syndrome and familial hypertriglyceridemia. In some embodiments, the disease is severe hypercholesterolemia. In some embodiments, the disease is homozygous/heterozygous familial hypercholesterolemia. In some embodiments the disease is hypertriglyceridemia.

Microsomal triglyceride transfer protein (MTP) is known to catalyze the transport of triglyceride and cholesteryl ester by preference to phospholipids such as phosphatidylcholine. It was demonstrated by D. Sharp et al., Nature (1993) 365:65 that the defect causing abetalipoproteinemia is in the MTP gene. This indicates that MTP is required for the synthesis of Apo B-containing lipoproteins such as VLDL, the precursor to LDL. It therefore follows that an MTP inhibitor would inhibit the synthesis of VLDL and LDL, thereby lowering levels of VLDL, LDL, cholesterol and triglyceride in humans.

MTP inhibitors belong to the class of polyarylcarboxamides. MTP inhibitors, methods of use and preparation thereof are known to the art skilled and are described, inter alia, in WO 96/26205; U.S. Pat. No. 5,760,246; WO 96/40640; WO-98/27979. Canadian Patent Application Ser. No. 2,091, 102, U.S. application Ser. No. 117,362, WO 92/26205 published Aug. 29, 1996, U.S. application Ser. No. 472,067, filed Jun. 6, 1995, U.S. application Ser. No. 548,811, filed Jan. 11, 1996, U.S. provisional application Ser. No. 60/017,224, filed May 9, 1996, U.S. provisional application Ser. No. 60/017, 253, filed May 10, 1996, U.S. provisional application Ser. No. 60/017,254, filed May 10, 1996, U.S. provisional application Ser. No. 60/028,216, filed Oct. 1, 1996, U.S. Pat. No. 5,595, 872, U.S. Pat. No. 5,789,197, U.S. Pat. No. 5,883,109, and U.S. Pat. No. 6,066,653. All of the above, including structures, are incorporated herein by reference.

Pharmacologic inhibition of MTP with Bristol-Myers Squibb's BMS-201038, a potent inhibitor of MTP, has been shown to reduce low density lipoprotein cholesterol (LDL-C) by up to 65% in healthy volunteers with hypercholesterolemia. Despite these impressive LDL-C reductions, steatorrhea, elevation of serum transaminases and hepatic fat accumulation were observed, primarily at 25 mg/day or higher doses. Thus, Bristol-Myers Squibb decided that these side effects made it unlikely that BMS-201038 could be developed as a drug for large scale use in the treatment of hypercholesterolemia. Combinations using MTP inhibitors and other cholesterol or triglyceride drugs have been previously disclosed (U.S. Pat. Nos. 6,066,653 and 5,883,109) but suffer the same drawbacks as described above for MTP inhibitors used alone.

In some embodiments the MTP inhibitors are piperidine, pyrrolidine or azetidine compounds. In some embodiments, the MTP inhibitor has a structure as set forth in U.S. Pat. No. 6,066,653. In some embodiments the MTP inhibitor is 9-[4-[4-[[2-(2,2,2-trifluoromethyl)-benzoyl]amino]-1-piperidinyl]butyl]-N-(2,2,2-trifluoroethyl)-9H-fluorene-9-carboxamide. In some embodiments, the MTP inhibitor is BMS-201038. As used herein, the phrase "BMS-201038" refers to a compound known as N-(2,2,2-Trifluorethyl)-9-[4-[4-[[[4'-(trifluoromethyl)[1,1'biphenyl]-2-Yl]carbonyl]amino]-1-piperidinyl]butyl]9H-fluorene-9-carboxamide, methanesulfonate, having the formula:

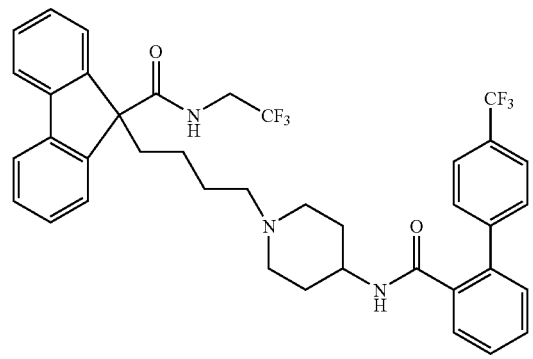

or a pharmaceutically acceptable salt thereof or the piperidine N-oxide thereof.

In some embodiments, MTP activity is inhibited by 10%, 20%, 25%, 30%, 40%, 50%, 60%, 70%, 75%, 80, 90%, 95%, or 100% compared to a MTP activity in an untreated or control subject. Methods for testing for inhibition of MTP activity are known to those of skill in the art and are set forth, for example, in U.S. Pat. No. 5,789,197.

As used herein, the phrase "untreated or control subject" refers to a subject who has not been administered an MTP inhibitor in at least three step-wise, increasing dosages.

In some embodiments, the methods further comprise the administration of other lipid modifying compounds. As used herein, the phrase "lipid modifying compounds" and the like, refers to medicaments for treating disorders associated with hypercholesterolemia and/or hyperlipidemia using standard dosing, e.g. a treatment not including at least three step-wise, increasing dosages of an MTP inhibitor. Lipid modifying compounds which may be used in the method of the invention include, without limitation, HMG CoA reductase inhibitors, cholesterol absorption inhibitors, ezetimide, squalene synthetase inhibitors, fibrates, bile acid sequestrants, statins, probucol and derivatives, niacin, niacin derivatives, PPAR alpha agonists, fibrates, PPAR gamma agonists, thiazolidinediones, and cholesterol ester transfer protein (CETP) inhibitors.

HMG CoA reductase inhibitors suitable for use herein include, but are not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171, with pravastatin, lovastatin or simvastatin being preferred. Other HMG CoA reductase inhibitors which may be employed herein include, but are not limited to, fluvastatin, rosuva, cerivastatin, atorvastatin, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)alkyl]pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-di-substituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, as well as other known HMG CoA reductase inhibitors. In addition, phosphinic acid compounds useful in inhibiting HMG CoA reductase suitable for use herein are disclosed in GB 2205837.

Squalene synthetase inhibitors suitable for use herein include, but are not limited to, α-phosphonosulfonates disclosed in U.S. application Ser. No. 08/266,888, filed Jul. 5, 1994 (HX59b), those disclosed by Biller et al, J. Med. Chem. 1988, Vol. 31, No. 10, pp 1869-1871, including isoprenoid (phosphinylmethyl)phosphonates including the triacids thereof, triesters thereof and tripotassium and trisodium salts thereof as well as other squalene synthetase inhibitors disclosed in U.S. Pat. Nos. 4,871,721 and 4,924,024 and in Biller et al, J. Med. Chem., 1988, Vol. 31, No. 10, pp 1869 to 1871.

In addition, other squalene synthetase inhibitors suitable for use herein include the terpenoid pyrophosphates disclosed by P. Ortiz de Montellano et al, J. Med. Chem.; 1977, 20, 243-249, the farnesyl diphosphate analog A and presqualene pyrophosphate (PSQ-PP) analogs as disclosed by Corey and Volante, (J. Am. Chem. Soc. 1976, 98, 1291-1293), phosphinylphosphonates reported by McClard, R. W. et al, (J.A.C.S., 1987, 109, 5544) and cyclopropanes reported by Capson, T. L., (PhD dissertation, June, 1987, Dept. Med. Chem. U. of Utah, Abstract, Table of Contents, pp. 16, 17, 40-43, 48-51, Summary). In some embodiments the inhibitor is pravastatin, lovastatin or simvastatin.

Peroxisome proliferator activated receptor-alpha (PPAR-alpha) and PPAR-gamma agonists, fibrates, thiazolidinediones and CETP inhibitors are well known to those skilled in the art.

The present invention provides methods for treating diseases or disorders associated with hyperlipidemia and/or hypercholesterolemia while minimizing side-effects ordinarily associated with the use of such inhibitors. In some embodiments, the inhibitor is an MTP inhibitor having the structure:

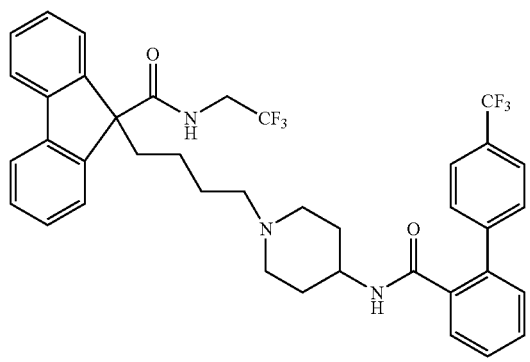

In some embodiments, one or more of total cholesterol levels, plasma LDL-cholesterol levels, triglyceride levels, fasting triglycerides (TG) levels, VLDL levels, lipoprotein (a) (Lp(a)) levels, or Apolipoproteins A-I, A-II, B, and E levels in the subject are reduced by at least 15%, by at least 25%, at least 30%, at least 40%, at least 50%, at least 60%, at least 70%, at least 75%, or at least 80% compared to control blood levels.

In some embodiments, triglyceride levels achieved are less than 500 mg/dl. In some embodiments, triglyceride levels achieved are less than 300 mg/dl. In some embodiments, triglyceride levels achieved are less than 200 mg/dl. In some embodiments, triglyceride levels achieved are less than 150 mg/dl.

In some embodiments, the ApoB/ApoA1 ratio achieved by treatment according to the present invention is from 0.25 to 1.25. In some embodiments the ApoB/ApoA1 ratio achieved is from 0.1 to 2.0. In some embodiments the apoB level achieved is from 48-130. In some embodiments the apoB level achieved is from 20-180.

As used herein, the phrase "control blood levels" refers to a level of a particular blood component in the absence of treatment according to the present invention. In some embodiments, the "control blood level" is the level of a particular blood component in the subject prior to treatment of the subject according to the present invention. In some embodiments, the "control blood level" is the level of a particular blood component if a subject either receiving a placebo or receiving a different treatment; e.g. a treatment not including at least three step-wise, increasing dosages of an MTP inhibitor. Reduction of levels of blood components, including, for example, cholesterol, triglycerides, and apolipoprotein B, can be determined by comparing pre-treatment levels to levels during or after treatment according to the present invention. Methods of measuring levels of particular components of blood are well-known to those of skill in the art. For example, total plasma cholesterol and triglyceride concentrations may be determined by a modification of the Liebermann-Burchard reaction (Abell L L, Levy B B, Brodie B B, Kendall F E. A simplified method for the estimation of total cholesterol in serum and demonstration of its specificity. *J Biol Chem.* 1952; 195:357-362) and by the method of Kessler and Lederer after zeolite extraction, (Kessler G, Lederer H. Fluorometric measurement of triglycerides. In: Skeggs LT, Jr, eds. *Automation in Analytical Chemistry: Technicom Symposia.* New York, N.Y.: Madiad Inc; 1965:341-344), respectively. Plasma HDL cholesterol may be estimated by the method of Allain et al (Allain C C, Poon L S, Chan G S G, Richmond W, Fu P C. Enzymatic determination of total serum cholesterol. *Clin Chem.* 1974; 20:470-475) using an enzymatic kit (Biotrol). LDL cholesterol may be calculated using the Freidewald formula. (Freidewald W T, Levy R I, Fredrickson D S. Estimation of the concentration of low density lipoprotein-cholesterol in plasma without the use of the preparative ultracentrifuge. *Clin Chem.* 1972; 18:499-502). Plasma apoB, apoA1, and lipoprotein(a) levels may be measured by immunological assays as described earlier (Guo H, Chapman M J, Bruckert E, Farriaux J P, De Gennes J L. Lipoprotein Lp(a) in homozygous familial hypercholesterolemia: density profile, particle heterogeneity and apolipoprotein(a) phenotype. *Atherosclerosis.* 1991; 31:69-83) and based on laser immunonephelometry (Immuno AG).

In some embodiments, the subject is a mammal, preferably a human. In some embodiments, the subject has proven refractory to previous treatment regimens.

The MTP inhibitors of the present invention may be used alone or optionally in combination with other lipid modifying compounds and may be administered systemically, such as orally or parenterally or transdermally, to subjects in need of treatment. The dosages and formulations for the other lipid modifying compounds to be employed, where applicable, will be as set out in the latest edition of the Physicians' Desk Reference.

As used herein, the term "susceptible" refers to patients who suffer one or more side-effects when MTP inhibitors are administered to them using traditional treatment regimens in an attempt to ameliorate hypercholesterolemia and/or hyperlipidemia.

As used herein, the phrase "traditional treatment regimens" and the like, refers to methods of treating hypercholesterolemia and/or hyperlipidemia using standard dosing, e.g. a treatment not including at least three step-wise, increasing dosages of an MTP inhibitor.

Although not wishing to be bound by theory, it is thought that the administration of MTP inhibitors in accordance with the methods of the present invention, in combination with one or more other lipid modifying compounds may further reduce undesired levels of cholesterol or lipids and/or reduce undesired side-effects of the MTP inhibitor or undesired side-effects of the MTP inhibitor and the other lipid modifying compounds.

In some embodiments, the MTP inhibitor is administered at escalating doses. In some embodiments, the escalating doses comprise at least a first dose level and a second dose level. In some embodiments, the escalating doses comprise at least a first dose level, a second dose level, and a third dose level. In some embodiments, the escalating doses further comprise a fourth dose level. In some embodiments, the escalating doses comprise a first dose level, a second dose level, a third dose level, a fourth dose level and a fifth dose level. In some embodiments, six, seven, eight, nine and ten dose levels are contemplated.

In some embodiments, each dose level is no more than 50% of the immediately following dose level. In some embodiments, each dose level is no more than 33% of the immediately following dose level. In some embodiments, each dose level is no more than 20% of the immediately following dose level. In some embodiments, dose levels are separated by ½ log units. In some embodiments, dose levels are separated by 1 log unit.

In some embodiments, the first dose level is from about 0.02 to about 0.059 mg/kg/day. In some embodiments, second dose level is from about 0.06 to about 0.19 mg/kg/day. In some embodiments, the third dose level is from about 0.2 to about 0.59 mg/kg/day. In some embodiments, the fourth dose level is from about 0.6 to about 2.0 mg/kg/day.

In some embodiments the MTP inhibitor is administered to the subject at:
(a) 0.03 mg/kg/day for a first interval;
(b) 0.1 mg/kg/day for a second interval;
(c) 0.3 mg/kg/day for a third interval; and
(d) 1.0 mg/kg/day for a fourth interval.

In some embodiments the first, second, third, and fourth dose levels are administered to the subject for from about 2 days to about 6 months in duration. In some embodiments the first, second, third, and fourth dose levels are administered to the subject for from about 7 days to about 35 days in duration. In some embodiments the first, second, third, and fourth dose levels are administered to the subject for from about 2 weeks to about 4 weeks in duration. In some embodiments the first, second, third, and fourth dose levels are administered to the subject for about 4 weeks. In some embodiments the first, second, third dose levels are administered to the subject for from about 2 days to about 40 days and the fourth dose level is administered to the subject for from about 2 days to about 6 months.

In some embodiments, the first dose level is from about 2 to about 30 mg/day. In some embodiments, the second dose level is from about 20 to about 50 mg/day. In some embodiments, the third dose level is from about 30 to about 60 mg/day. In some embodiments, the fourth dose level is from about 40 to about 75 mg/day. In some embodiments, the fifth dose level is from about 50 to about 75 mg/day.

In some embodiments, the first dose level is from about 2 to about 13 mg/day. In some embodiments, the second dose level is from about 5 to about 30 mg/day. In some embodiments, the third dose level is from about 10 to about 50 mg/day. In some embodiments, the fourth dose level is from about 20 to about 60 mg/day. In some embodiments, the fifth dose level is from about 30 to about 75 mg/day.

In some embodiments the first dose level is 6.25 mg/day, the second dose level is 12.5 mg/day, and the third dose level is 50 mg/day.

In some embodiments the first dose level is about 12.5 mg/day. In some embodiments, the second dose level is about 25 mg/day. In some embodiments, the third dose level is from about 37.5 mg/day. In some embodiments, the fourth dose level is about 50 mg/day.

In some embodiments the first dose level is about 25 mg/day. In some embodiments, the second dose level is about 37.5 mg/day. In some embodiments, the third dose level is from about 50 mg/day. In some embodiments, the fourth dose level is about 75 mg/day.

In some embodiments the methods comprise the administration of five or more escalating doses to the subject. In some embodiments the first dose level is 6.25 mg/day, the second dose level is 12.5 mg/day, the third dose level is 25 mg/day, the fourth dose level is 37.5 mg/day, and the fifth dose level is 50 mg/day.

In some embodiments each dose level is administered to the subject for from 2 days to 26 weeks. In some embodiments each dose level is administered to the subject for from about 1 week to about 26 weeks. In some embodiments each dose level is administered to the subject for from about 1 week to about 12 weeks. In some embodiments, each dose level is administered to the subject for 1 week to 5 weeks. In some embodiments each dose level is administered to the subject from 1 to 4 weeks. In some embodiments each dose level is administered to the subject from 1 to 2 weeks. In some embodiments each dose level is administered to the subject from 1 to 2 weeks.

In some embodiments the first dose level is administered to the subject for 1 week, the second dose level is administered to the subject for 1 week, and the third dose level is administered to the subject for 1 week.

In some embodiments the first dose level is administered to the subject for 2 weeks, the second dose level is administered to the subject for 2 weeks, and the third dose level is administered to the subject for 2 weeks.

In some embodiments, the other lipid modifying compounds are administered according to traditional treatment regimens. In some embodiments, the lipid modifying compounds are administered at escalating doses. In some embodiments, the lipid modifying compounds are administered to the subject in least three step-wise, increasing dosages.

As used herein, the phrase "minimizing side effects" refers to an amelioration or elimination of one or more undesired side effects of the MTP inhibitors of the present invention.

As used herein, the phrase "side effects" refers to undesired events occurring as a result of the traditional use of the inhibitors of the invention. "Side effects" of traditional use of the MTP inhibitors include, without limitation, steatorrhea, abdominal cramping, distention, elevated liver function tests, fatty liver; hepatic fat build up, polyneuropathy, peripheral neuropathy, rhabdomyolysis, arthralgia, myalgia, chest pain, rhinitis, dizziness, arthritis, peripheral edema, gastroenteritis, liver function tests abnormal, colitis, rectal hemorrhage, esophagitis, eructation, stomatitis, biliary pain, cheilitis, duodenal ulcer, dysphagia, enteritis, melena, gum hemorrhage, stomach ulcer, tenesmus, ulcerative stomatitis, hepatitis, pancreatitis, cholestatic jaundice, paresthesia, amnesia, libido decreased, emotional lability, incoordination, torticollis, facial paralysis, hyperkinesia, depression, hypesthesia, hypertonia, leg cramps, bursitis, tenosynovitis, myasthenia, tendinous contracture, myositis, hyperglycemia, creatine phosphokinase increased, gout, weight gain, hypoglycemia, anaphylaxis, angioneurotic edema, and bullous rashes (including erythema multiforme, Stevens-Johnson syndrome, and toxic epidermal necrolysis). In some embodiments, side effects are partially eliminated. As used herein, the phrase partially eliminated refers to a reduction in the severity, extent, or duration of the side effect of at least 25%, 50%, 75%, 85%, 90%, or preferably 95%. In some embodiments, side effects are completely eliminated. Those skilled in the art are credited with the ability to detect and grade the severity, extent, or duration of side effects as well as the degree of amelioration of a side effect. In some embodiments, two or more side effects are ameliorated.

In some embodiments, the methods of the present invention minimize GI side effects or hepatobiliary side effects. In some embodiments, the methods minimize at least one of steatorrhea, abdominal cramping, distention, elevated liver function tests, minor fatty liver; hepatic fat build up, polyneuropathy, peripheral neuropathy, rhabdomyolysis, arthralgia, myalgia, chest pain, rhinitis, dizziness, arthritis, peripheral edema, gastroenteritis, liver function tests abnormal, colitis, rectal hemorrhage, esophagitis, eructation, stomatitis, biliary pain, cheilitis, duodenal ulcer, dysphagia, enteritis, melena, gum hemorrhage, stomach ulcer, tenesmus, ulcerative stomatitis, hepatitis, pancreatitis, cholestatic jaundice, paresthesia, amnesia, libido decreased, emotional lability, incoordination, torticollis, facial paralysis, hyperkinesia, depression, hypesthesia, hypertonia, leg cramps, bursitis, tenosynovitis, myasthenia, tendinous contracture, myositis, hyperglycemia, creatine phosphokinase increased, gout, weight gain, hypoglycemia, anaphylaxis, angioneurotic edema, and bullous rashes (including erythema multiforme, Stevens-Johnson syndrome, and toxic epidermal necrolysis).

In some embodiments, minimization of one or more side effects occurs within 2 weeks of initiation of treatment. In some embodiments, minimization of the one or more side effects occurs within 3 weeks of initiation of treatment.

In some embodiments the minimization of the side effect is determined by assessing the grade, severity, extent, or duration by subject questionnaire.

The present invention also provides methods for inhibiting MTP in a subject while reducing side effects comprising administering to the subject an amount of an MTP inhibitor effective to inhibit MTP. In some embodiments, the MTP inhibitor is administered orally.

The present invention further provides a kit for treating a disorder associated with hyperlipidemia and/or hypercholesterolemia in a subject. In some embodiments the kit comprises at least three sets of dosage units of an MTP inhibitor, wherein a first set of dosage units provides 0.03 mg/kg/day for a first interval, a second set of dosage units provides 0.1 mg/kg/day for a second interval, and a third set of dosage units provides 0.3 mg/kg/day for a third interval; and b) instructions for use. In some embodiments, the kit further comprises a fourth set of dosage units, said fourth set providing 1.0 mg/kg/day for a fourth interval. In some embodiments, the kit further comprises a container for storing the sets of dosage units according to a schedule for administration.

In some embodiments, the kit comprises a first set of dosage units providing 6.25 mg/day for a first interval, a second set of dosage units providing 12.5 mg/day for a second interval, a third set of dosage units providing 25 mg/day for a third interval, a fourth set of dosage units providing 37.5 mg/day for a fourth interval, and a fifth set of dosage units providing 50 mg/day for a fifth interval.

Each set of dosage units comprises sufficient dosage units to administer a desired dosage to the subject for the duration of the period for the specific dose. For example, if a dosage level of 25 mg/day is to be administered to the subject for 2 weeks, the set of dosage units for the 25 mg/day may include 14 dosage units of 25 mg. Alternatively, the set may include 70 dosage units of 5 mg.

In some embodiments the kit further comprises one or more further lipid modifying compounds for the treatment of a disorder associated with hyperlipidemia and/or hypercholesterolemia.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

The dose administered may be adjusted according to age, weight and condition of the patient, as well as the route of administration, dosage form and regimen and the desired result. In some embodiments, doses administered to the subject are titrated until a desired endpoint is reached.

Preparation and formulations of the inhibitors are disclosed infra, supra, and in Canadian Patent Application Ser. No. 2,091,102; U.S. application Ser. No. 117,362; WO 92/26205 published Aug. 29, 1996; U.S. application Ser. No. 472,067, filed Jun. 6, 1995; U.S. application Ser. No. 548,811, filed Jan. 11, 1996; U.S. provisional application Ser. No. 60/017,224, filed May 9, 1996; U.S. provisional application Ser. No. 60/017,253, filed May 10, 1996; U.S. provisional application Ser. No. 60/017,254, filed May 10, 1996; U.S. provisional application Ser. No. 60/028,216, filed Oct. 1, 1996; U.S. Pat. No. 5,595,872, U.S. Pat. No. 5,712,279; U.S. Pat. No. 5,739,135; U.S. Pat. No. 5,789,197, U.S. Pat. No. 5,883,109, and U.S. Pat. No. 6,066,653. All of the above, including structures, are incorporated herein by reference.

For oral administration, a satisfactory result may be obtained employing the MTP inhibitor in a daily amount within the range of from about 0.01 mg/kg to about 100 mg/kg and preferably from about 0.1 mg/kg to about 75 mg/kg, one to four times daily.

For parenteral administration, the MTP inhibitor may be employed in a daily amount within the range of from about 0.005 mg/kg to about 10 mg/kg and preferably from about 0.005 mg/kg to about 8 mg/kg, one to four times daily.

Additional lipid modifying compounds, when present, may be employed in dosages normally employed as indicated in the Physician's Desk Reference, for each of such agents such as in an amount within the range of from about 2 mg to about 7500 mg, from about 2 mg to about 4000 mg, or from about 10 mg to about 5000 mg.

The MTP inhibitor and other lipid modifying compounds may be employed together in the same oral dosage form or in separate oral dosage forms taken at the same time.

The compositions described above may be administered in the dosage forms as described above in single or divided doses of one to four times daily.

Dosage units including tablets, capsules and caplets, of various sizes can be prepared, e.g., of about 2 to 10000 mg in total weight, containing one or both of the active substances in the ranges described above, with the remainder being a physiologically acceptable carrier of other materials according to accepted pharmaceutical practice. These tablets can, of course, be scored to provide for fractional doses. Gelatin capsules can be similarly formulated.

In some embodiments, the MTP inhibitor and other lipid modifying compounds are provided in the same dosage unit in the form of a divisible dosage unit. For example, in some embodiments a scored tablet may provide the dosage unit. Under the direction of a physician or other medical professional, the subject may be directed to take one portion of the dosage unit, wherein the one portion will provide the desired dosage level for given interval. At the following interval, the patient may be instructed to take two or more portions of the dosage unit wherein the two or more portions will provide the desired dosage level for that interval.

Liquid formulations can also be prepared by dissolving or suspending one or the combination of active substances in a conventional liquid vehicle acceptable for pharmaceutical administration so as to provide the desired dosage in one to four teaspoonsfuls.

Such dosage forms can be administered to the patient on a regimen of one to four doses per day.

According to some embodiments, in order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

Fixed combinations of MTP inhibitors and other lipid modifying compounds are more convenient and are preferred, especially in tablet or capsule form for oral administration.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the carrier, glycerol as solubilizer, sucrose as sweetening agent, methyl and propyl parabens as preservatives, a dye and a flavoring such as cherry or orange.

Some of the active substances described above form commonly known, pharmaceutically acceptable salts such as alkali metal and other common basic salts or acid addition salts, etc. References to the base substances are therefore intended to include those common salts known to be substantially equivalent to the parent compound.

The formulations as described above will be administered for a prolonged period, that is, for as long as the acid lipase deficiency exists. Sustained release forms of such formulations which may provide such amounts biweekly, weekly, monthly and the like may also be employed.

The following examples are meant to illustrate the invention and are not to be construed to limit the invention in any way. Those skilled in the art will recognize modifications that are within the spirit and scope of the invention.

EXAMPLES

Example 1

Formulations suitable for oral administration are prepared as described below.

Capsules containing 1 mg MTP inhibitor BMS 201,038 and capsules containing 50 mg BMS 201,038 are produced from the following ingredients.

|  | 1 mg capsule<br>Amt (mg/capsule) | 50 mg capsule<br>Amt (mg/capsule) |
|---|---|---|
| BMS-201038* | 1.1 | 56.9 |
| Lactose, Hydrous, NF | ca. 30.2 | ca. 99.9 |
| Lactose, Anhydrous, NF | 47.3 | 0.0 |
| Microcrystalline Cellulose, NF | 10.0 | 50.0 |
| Pregelatinized Starch, NF | 5.0 | 25.0 |
| Sodium Starch Glycolate, NF | 5.0 | 12.5 |
| Colloidal Silicon Dioxide, NF | 1.0 | 5.0 |
| Magnesium Stearate, NF | 0.3 | 0.6 |
| Purified Water, USP or | q.s. | q.s. |
| Water for Injection, USP | q.s. | q.s. |
| Gray, Opaque, Size #0 | One Capsule | One Capsule |
| Total Fill Weight | 100.0 | 250.0 |

*In the 1 mg capsule this amount is expressed in terms of the amount of methane sulfonic acid salt per capsule at 100% potency. In the 50 mg capsule, this amount is expressed in terms of the free base This is equivalent to 1 mg and 50 mg (1 mg capsule and 50 mg capsule, respectively) of the free base.

The MTP inhibitor BMS 201,038, and colloidal silicon dioxide are blended in a suitable blender with lactose hydrous, microcrystalline cellulose, pregelatinized starch and a portion of sodium starch glycolate. The resulting blend is wet granulated with water. The wet granulation is dried in a suitable dryer. The remaining portion of sodium starch glycolate is added to the granulation and mixed therein. Magnesium stearate is added to the granulation and mixed therein. The resulting blend is filled into capsules.

Example 2

Pravastatin tablets (10, 20 or 40 mg as described in the 2004 PDR) and MTP inhibitor (BMS 201,238) tablets may be administered as a combination in accordance with the teachings of the present invention. In addition, the pravastatin and MTP inhibitor tablets may be ground up into powders and used together in a single capsule.

Example 3

Simvastatin tablets (10, 20 or 40 mg as described in the 2004 PDR) and MTP inhibitor (BMS 201,238) tablets may be administered as a combination in accordance with the teachings of the present invention. In addition, the simvastatin and MTP inhibitor tablets may be ground up into powders and used together in a single capsule, caplet or tablet.

Example 4

Ezetimibe tablets (10 mg as described in the 2004 PDR) and MTP inhibitor (BMS 201,238) tablets may be administered as a combination in accordance with the teachings of the present invention. In addition, the ezetimibe and MTP inhibitor tablets may be ground up into powders and used together in a single capsule, caplet or tablet.

Example 5

Tablets containing 500 mg clofibrate by itself or in combination with 10 mg BMS 201,038 may be employed in separate dosage forms or combined in a single capsule form.

Example 6

To evaluate pharmacodynamic readouts of treatment according to the present invention, the effects of treatment with BMS-201038 at 4 dose levels (0.03, 0.1, 0.3, and 1.0 mg/kg body weight) on nutritional status, hepatic fat content and pulmonary function can be determined by:
(a) Hepatic fat content as measured by MRI\nuclear magnetic resonance spectroscopy (NMRS);
(b) Pulmonary function as measured by spirometry with DLCO;
(c) Nutritional status as measured by serum levels of fat soluble vitamins A, D, and E;
(d) international normalized ratio (INR) to evaluate vitamin K status; and plasma phospholipid inoleic acid, arachidonic acid, alpha linolenic acid and eicosapentaenoic acid by gas liquid chromatography to assess essential fatty acid intake.

Example 7

Twenty (20) subjects are randomized in a 3:1 ratio to BMS-201038 (n=15) or placebo (n=5) in a double-blind fashion for 11-15 weeks depending on weight as described below. At the end of 11 or 15 weeks, BMS-assigned subjects will continue taking the maximum tolerated dose for the remaining study (through week 39). For BMS-201038-treated patients, study drug will be initiated at 6.25 mg/d for 1 week and then will be titrated up to 12.5 mg/day for 2 weeks followed by 25 mg/day for 4 weeks and then to 50 mg/day for 4 weeks. BMS-201038 treated subjects whose weight is between 62.5 and 74.9 kg will titrate up to 62.5 mg/day for an additional 4 weeks. BMS-201038-treated subjects whose weight is $\geq$75 kg, will titrate up from 50 mg to 75 mg/day for an additional 4 weeks. Subjects who weight is <62.5 kg will remain at 50 mg/d (or the maximum tolerated dose) for the remaining 28 weeks. Subjects who titrate up to 62.5 mg/d or 75 mg/day will remain at this dose (or the maximum tolerated dose) for the remaining 24 weeks.

Subjects randomized to placebo will take matching placebo for 15 weeks. After this time period, placebo-treated subjects will start taking BMS-201038 following the same schedule as outlined above for the original BMS-201038-treated subjects. After the dose titration schedule is complete at week 26 or 30 depending on weight, subjects will take the maximum tolerated dose for the remaining study (through week 39) so that the entire study for all subjects will be 39 weeks in duration.

Example 8

The tolerability and thus the effectiveness of BMS-201038 appears to be dependent on the dosing regimen. In a phase II study using BMS-201038 in patients with primary hypercholesterolemia, a dosage of 25 mg per day for 4 weeks produced clinically significant gastrointestinal (GI) steatorrhea, abdominal cramping and distention) and statistically significant hepatobiliary (elevated liver function tests and minor fatty liver) symptoms in some patients receiving study drug. It appeared that the degree of both GI-related symptoms and hepatic fat were in part due to the study design, particularly the dosing regimen. BMS-201038 is a potent inhibitor of both intestinal and hepatic microsomal triglyceride transfer protein (MTP). While lack of adequately controlling dietary fat intake most likely contributed to GI-related symptoms, it is possible that providing a starting dose of 25 mg/day also contributed. Starting at a low dose and titrating up slowly may improve GI-related tolerability as well as provide time for the liver to adjust to the inhibition of MTP, perhaps decreasing hepatic fat build up. This theory was applied in designing a study investigating the safety, tolerability and efficacy of BMS-201038 in patients with homozygous familial hypercholesterolemia (hoFH).

Six patients with hoFH were enrolled and completed the study per protocol. Subjects received once daily dosing of 4 doses of BMS-201038 (0.03, 0.1, 0.3 and 1.0 mg/kg) for 4 weeks at each dose. We chose an initial low dose (0.03 mg/kg) that while not expecting to be efficacious, would be a dose that would be expected to be safe and well tolerated (~2.1 mg in the 70 kg man). The remaining three doses were chosen by calculating ½ log units of the previous dose. We picked an upper dose of 1 mg/kg based on data from the animal study by Wetterau and colleagues revealing greater than 80% LDL cholesterol reduction using 10 mg/kg, with an $ED_{50}$ of 1.9 mg/kg. All 6 subjects tolerated the drug up to the maximal 1 mg/kg dose with little to no steatorrhea. Although all subjects had evidence of dose-dependent increases in hepatic fat by NMRS, the increase from baseline to 4 weeks on 1 mg/kg was varied with a range of 3-37%. Three of 6 subjects experienced substantial increases in liver transaminases, but only 1 subject had a persistent increase that required a temporary dose reduction. This subject also had the greatest increase in hepatic fat which may have been exacerbated by the large consumption of alcohol on a regular basis. At the two highest doses, the mean percent changes in lipids among the 6 subjects were: total cholesterol −30±9% and −58±8.5%, non-HDL cholesterol −31±9% and −60±8.8%, and apoB −15±16% and −55±13%, respectively. These data indicate that symptoms of steatorrhea and hepatic fat can be significantly reduced by initiating a low dose with a gradual up titration.

Each of the patents, patent applications, references and publications described herein is hereby incorporated by reference in its entirety.

Various modifications of the invention, in addition to those described herein, will be apparent to those of skill in the art in view of the foregoing description. Such modifications are also intended to fall within the scope of the appended claims.

What is claimed is:

1. A method of treating a subject suffering hyperlipidemia or hypercholesterolemia, the method comprising administering to the subject an effective amount of an MTP inhibitor, wherein said administration comprises at least three stepwise, increasing dose levels of the MTP inhibitors wherein a first dose level is from about 2 to about 13 mg/day, a second dose level is from about 5 to about 30 mg/day, and a third dose level is from about 10 to about 50 mg/day; and wherein the MTP inhibitor is represented by:

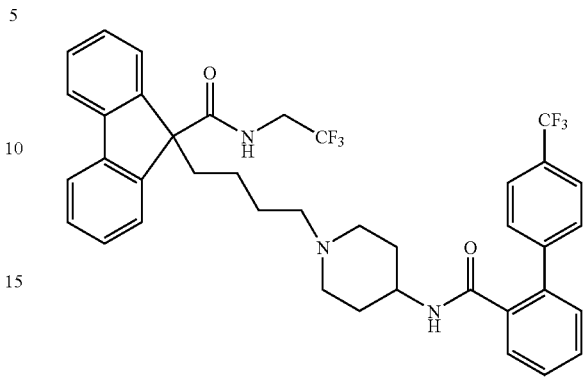

or a pharmaceutically acceptable salt thereof or the piperidine N-oxide thereof, and wherein each dose level is administered to the subject for about 1 to 4 weeks.

2. The method of claim 1 wherein the disorder is severe hypercholesterolemia.

3. The method of claim 1 wherein one or more of Total Cholesterol, LDL, fasting triglycerides (TG), VLDL, lipoprotein (a) (Lp(a)), and-lipoprotein B are reduced by at least 15%, compared to control levels.

4. The method of claim 1 wherein one or more of Total Cholesterol, LDL, fasting triglycerides (TG), VLDL, lipoprotein (a) (Lp(a)), and-lipoprotein B are reduced by at least 25%, compared to control levels.

5. The method of claim 1 wherein the MTP inhibitor is administered orally.

6. The method of claim 1 wherein said increasing dose levels further comprise a fourth dose level.

7. The method of claim 1 wherein said increasing dose levels further comprise a fourth and a fifth dose level.

8. The method of claim 1, wherein the increasing dose levels comprise a fourth dose level from about 20 to about 60 mg/day and a fifth dose level from about 30 to about 75 mg/day.

* * * * *

UNITED STATES PATENT AND TRADEMARK OFFICE
CERTIFICATE OF CORRECTION

PATENT NO. : 7,932,268 B2
APPLICATION NO. : 10/591923
DATED : April 26, 2011
INVENTOR(S) : Daniel J. Rader Page 1 of 1

It is certified that error appears in the above-identified patent and that said Letters Patent is hereby corrected as shown below:

Claim 1, column 19, line 40, between "suffering" and "hyperlipidemia" insert --from--.

Signed and Sealed this
Seventeenth Day of January, 2012

David J. Kappos
*Director of the United States Patent and Trademark Office*